(12) United States Patent
Jeffery

(10) Patent No.: US 9,907,690 B1
(45) Date of Patent: Mar. 6, 2018

(54) ARTICULATION AID

(71) Applicant: Lisa Cheryl Jeffery, Miami, FL (US)

(72) Inventor: Lisa Cheryl Jeffery, Miami, FL (US)

(*) Notice: Subject to any disclaimer, the term of this patent is extended or adjusted under 35 U.S.C. 154(b) by 0 days.

(21) Appl. No.: 15/133,171

(22) Filed: Apr. 19, 2016

Related U.S. Application Data

(63) Continuation of application No. 14/189,977, filed on Feb. 25, 2014, now abandoned.

(60) Provisional application No. 61/768,591, filed on Feb. 25, 2013.

(51) Int. Cl.
| | |
|---|---|
| *A61B 10/00* | (2006.01) |
| *A61H 99/00* | (2006.01) |
| *G10L 15/00* | (2013.01) |
| *A61F 5/58* | (2006.01) |
| *G09B 19/04* | (2006.01) |

(52) U.S. Cl.
CPC ............... *A61F 5/58* (2013.01); *G09B 19/04* (2013.01)

(58) Field of Classification Search
CPC ... A61F 5/58; A61F 5/01; A61F 5/566; G09B 19/04
See application file for complete search history.

(56) References Cited

U.S. PATENT DOCUMENTS

| | | | | |
|---|---|---|---|---|
| 4,513,014 A * | 4/1985 | Edwards | ............. | A01K 15/026 119/710 |
| 6,202,598 B1 * | 3/2001 | Willinger | ............. | A01K 15/026 119/709 |

OTHER PUBLICATIONS

Boomerang Tags website (2008) accessed from Wayback Machine Internet Archive.*

* cited by examiner

*Primary Examiner* — Christine H Matthews
*Assistant Examiner* — Joshua D Lannu
(74) *Attorney, Agent, or Firm* — Jeffrey Roddy

(57) ABSTRACT

An articulation aid with seats for upper and lower teeth for positioning between the upper central incisors and the lower central incisors respectively, or upper lateral incisors to lower lateral incisors as the case may be resulting in a generally vertical orientation of the article prizing the jaw in an open position. The slender aid permits a user or voice therapist to discern the instant position of the tongue when the user is speaking.

3 Claims, 3 Drawing Sheets

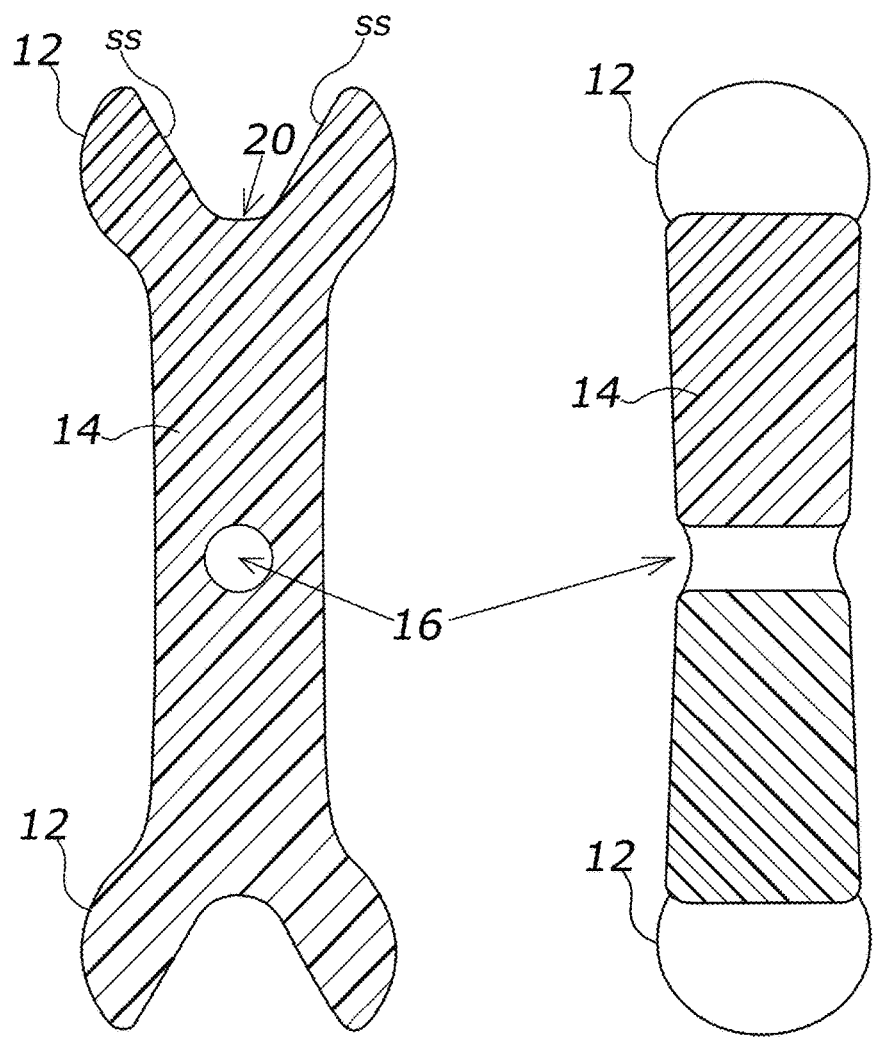

ARTICULATION AID

CROSS REFERENCE TO RELATED APPLICATIONS

This Application is a Continuation of U.S. Non-Provisional application Ser. No. 14/189,977 filed Feb. 25, 2014 titled "Articulation Aid" which claims the benefit of U.S. Provisional Patent Application No. 61/768,591 filed Feb. 25, 2013

BACKGROUND OF THE INVENTION

Field of the Invention

The instant invention relates generally to an article held between the front teeth as an aid to improving voice and speech characteristics.

Related Art

Various articles for improving speech characteristics have been described in the past. The so-called "bone prop" refers to any article; not necessarily a bone, which is held between the teeth to maintain the jaw in an open position and is known to acting circles. U.S. Pat. No. 7,214,064 to Hall sets forth an implement that is placed in the mouth between the teeth to assist in the development of proper articulation, and sound production. While the aforementioned devices have benefits, problems remain. Often the size of the device obstructs the view into the mouth making it difficult for speech therapists or voice coaches to determine the placement of the tongue when certain sounds are produced. Another issue arising from large articles placed in the mouth is damage to the gum line and oral mucosa. What is needed is a small article capable of maintaining the required space between the upper and lower front teeth so as to provide instant feedback on tongue position. It would be desirable for such an article to be thin, slightly flexible and shatter resistant, and to have a secure recessed seat or notch for upper and lower teeth to avoid accidental separation and falling away of the device when making slight jaw adjustments.

SUMMARY

In an aspect of the instant invention, an aid for improving speech characteristics such as articulation, tongue control and jaw musculature includes an article having a relatively elongated middle portion with a bulbous portion at each end. The bulbous portions are partially spherical with no sharp edges and possess a cut-away or notch that resembles a v-shape with a trough between the sloping sides (ss) of the v-shape notch which are shaped and sized for the seating of the upper and lower teeth. The notches typically seat between the upper central incisors and the lower central incisors respectively, or upper lateral incisors to lower lateral incisors as the case may be resulting in a generally vertical orientation of the article prising the jaw in an open position. Because the article is small, a string or ribbon that hangs outside the mouth is attached to the article so that the article can be recovered if taken into the mouth. When inserted between the teeth, the jaw is opened to the extent that articulation is made only with some effort. Use of the article exercises and builds the jaw musculature enabling the user to articulate correctly with considerably less effort once it is removed. Many users having a lisp that dentalize their 't', thus producing a 'th' sound by pushing their tongue excessively forward, are able to self correct once they directly observe their tongue placement while speaking. For others such as native Spanish speakers, who continue to roll their 'r' when speaking English, the article likewise enables direct observation of the tongue so that a conscious adjustment can be made and practiced.

Preferably, the article is constructed of a thermoplastic that is tough enough to withstand the flexing to the jaw without shattering, but that will not damage the seated teeth. Preferred materials include, but are not limited to, polypropylene, polyethylene and nylon.

Benefits of the instant invention include, but are not limited to (1) instant feedback of tongue position by user or coach/observer, (2) improves tongue musculature, (3) improves articulation, and (4) enables the user to produce the desired sounds without opening the mouth too wide.

The instant invention is small enough to be carried in a shirt pocket or purse, and with an attached ribbon or string can be carried about the neck without drawing attention.

The foregoing and other objects, features, and advantages of the invention will become more apparent from the following detailed description, which proceeds with reference to the accompanying figures.

BRIEF DESCRIPTION OF THE DRAWINGS

FIG. 4 is a cross-sectional view taken along lines 4'-4' of (FIG. 1);

FIG. 5 is a cross-sectional view taken along lines 5'-5' of (FIG. 2);

DETAILED DESCRIPTION OF THE INVENTION

Figures 1, 2:
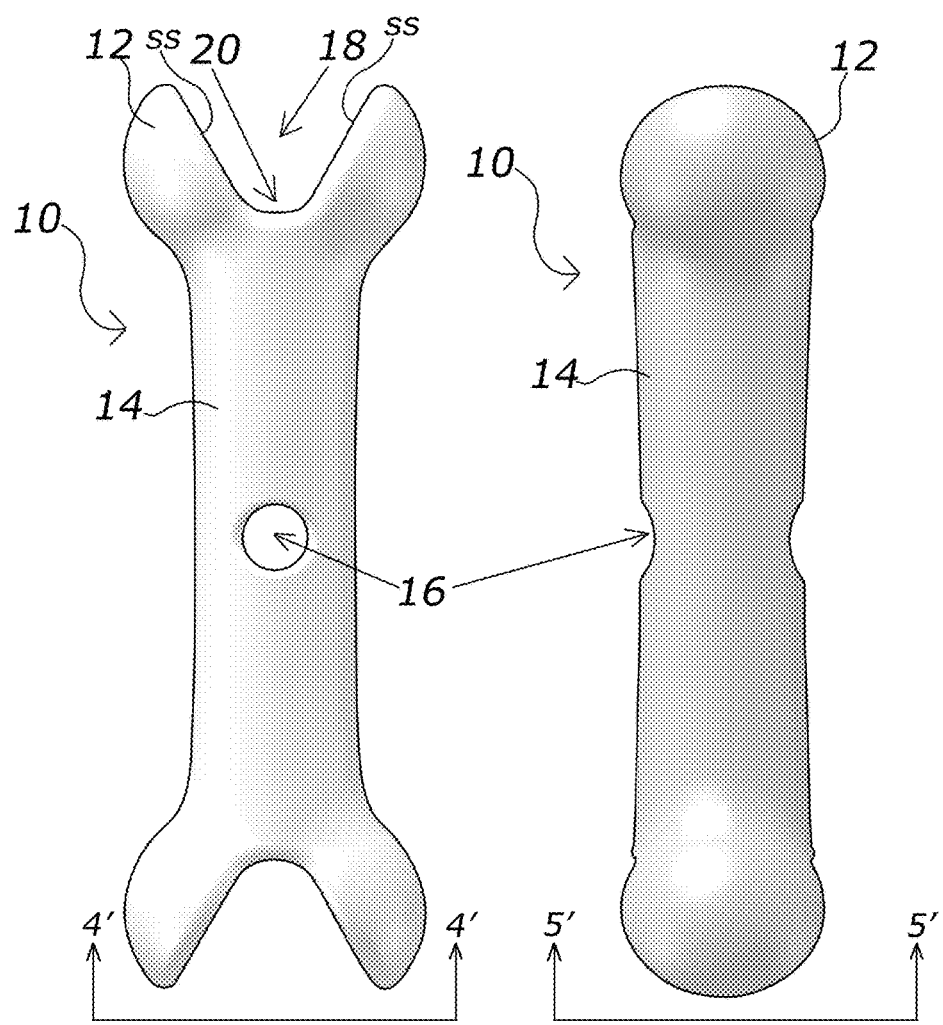
FIG. 1 is a perspective side view of a preferred embodiment of a voice training aid.
FIG. 2 is a perspective view thereof rotated 90° longitudinally.

Reference Listing 10 voice training aid
12 bulbous portion
14 midsection
16 aperture
18 seat
20 trough
21 ribbon

Definitions

In the following description, the term "aid" refers to articles used in any exercise or corrective process for improving speech characteristics. Unless otherwise explained, any technical terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." Publications, patent applications, patents, and other references mentioned herein, if any, are incorporated by reference in their entirety for all purposes. In case of conflict, the instant specification, including explanations of terms, will control. In addition, the materials, methods, and examples are illustrative only and not intended to be limiting.

Figure 3:
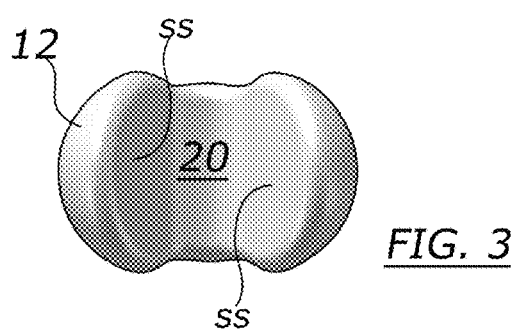
FIG. 3 is a perspective end view thereof.
Figure 6:
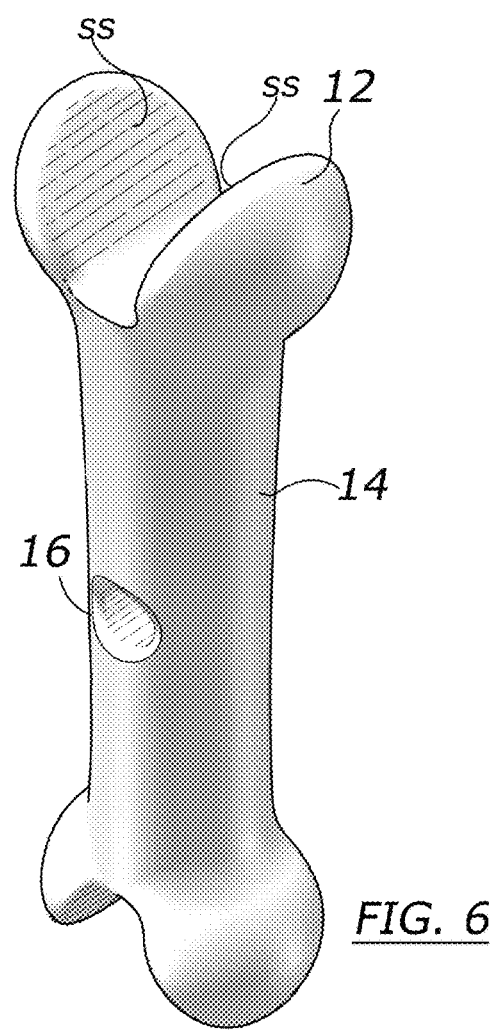
FIG. 6 is another perspective view thereof with a penny in dotted line to indicate scale.
Figure 7:
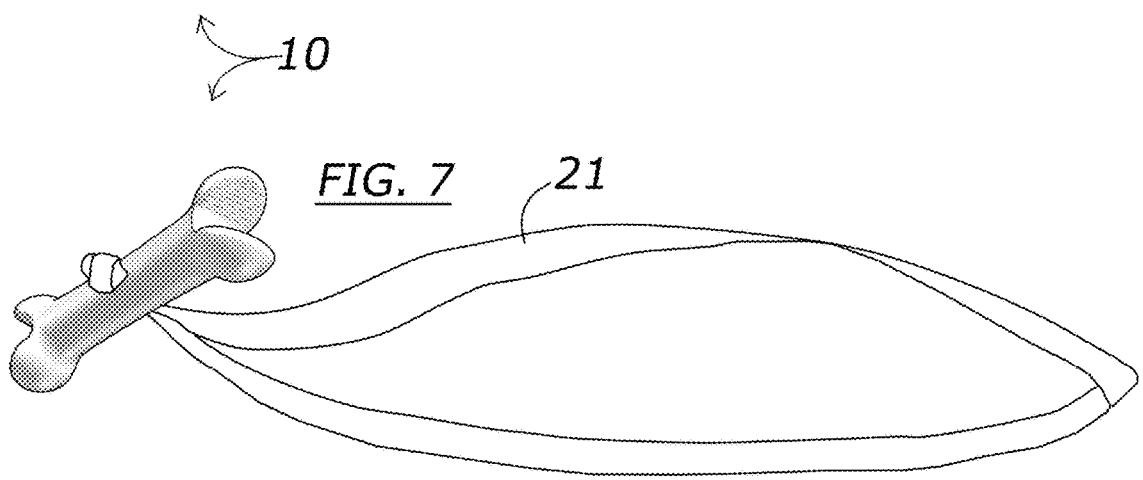
FIG. 7 is a reduced size perspective view thereof depicting a ribbon as a securing means.

Referring generally to FIGS. 1-7 an article for voice training and speech therapy includes a midsection 14 with a split bulbous portion 12 at each end. A recessed seat 18 in each bulbous portion possesses a trough 20 for seating of the upper or lower incisors when retained in a vertical orientation spanning the upper central and lower central incisors. This arrangement results in 4 semi-spherical lobes; 2 at each end of the article, on either side of the split bulbous portion. It should be noted that the lobes have a rounded aspect best shown in (FIGS. 2 and 3) that prevents damage to the teeth when retained, or to the gum line if accidentally dislodged. The articulation aid can be constructed of a single thermoplastic, or the ends can be made, coated, or over molded with a soft elastomer such as a silicone or urethane between 30 and 90 shore A that will conform to the edges of the engaged teeth.

Preferably, aperture 16 is formed in the midsection 14 for placement of a ribbon 21 or string therethrough in order to better retain the article and prevent possible choking.

For use with adults, preferably the length of the article of the instant invention is between 0.50 inch and 1 inch, and more preferably between 0.75 inch and 1 inch. Preferably the widest portion is between 0.3125 inch and 0.25 inch. Preferably, each lobe of the bulbous portions 12 is between 0.1875 inch and 0.25 inch in width. The length of midsection 14 is preferably between 0.375 and 0.5 inch. The diameter of the midsection is preferably between 0.125 inch and 0.15625 inch. The ratio between the midsection 14 diameter and the midsection length, combined with the already mentioned preferred materials, results in a slightly flexible article that helps mitigate jaw fatigue, and stays in place despite small jaw adjustments, e.g., altering the jaw span plus or minus the midsection length. Notably, the midsection is thin enough that a voice therapist can note the placement of the tongue which is critical for diagnosing speech irregularities caused by poor tongue placement. This feature is useful for teaching foreign languages which have different tongue placement than English.

In order to practice the instant invention, the article is placed between the upper and lower teeth, with the upper recesses or notches seated between the upper central and lower central incisors. Once the article is vertically oriented, selected words and phrases are spoken in order to assist the user with articulation especially that impacted by incorrect tongue placement. The letters 'd', 't', 'r', 'l' and 'n' are particularly stressed. It should be noted that the instant invention, unlike other mouth placed articles, does not physically constrain the tongue in any way; and operates primarily through visual feedback regarding the position of the tongue. Once instructed in the use of the instant invention, an individual can practice alone in front of a mirror to improve his/her articulation with or without the assistance of a language coach or speech therapist.

In view of the many possible embodiments to which the principles of the disclosed invention may be applied, it should be recognized that the illustrated embodiments are only preferred examples of the invention and should not be taken as limiting the scope of the invention. Therefore, this disclosure is intended to cover such alternatives, modifications, and equivalents as may be included in the spirit and scope of the description in view of the appended drawings and claims.

What is claimed is:

1. An article for improving speech characteristics comprising:
   (1) a radially symmetrical midsection including a midsection diameter between 0.125 inch and 0.15625 inch, the midsection is located between two bulbous portions, each bulbous portion is formed at opposite terminal ends of the midsection and wherein each of the two bulbous portions include two rounded lobes with an indentation between each of the two rounded lobes, each indentation includes a pair of sloping sides that include flat surfaces angularly opposed to one another and a trough, each trough includes a floor with a width sufficient for direct contact with an upper or lower incisor and the floor of each trough is located between the sloping sides and adapted for seating of upper or lower teeth of a human user, and,
   (2) wherein the article includes an overall length of between 0.5 inch and 1 inch in length, the article is configured to be placed in a mouth of the user and separate the upper teeth from the lower teeth of the user as part of a speech therapy or voice training exercise, and the article is further configured to permit articulation of the user's tongue during speech exercises and visual feedback regarding an instant position of the user's tongue which is observable behind the article when held between the upper and lower teeth.

2. The article according to claim 1 with a through aperture within the midsection midway between the two bulbous portions.

3. The article according to claim 1 wherein the article is rigid plastic.

* * * * *